US009629599B2

(12) United States Patent
Jerebko et al.

(10) Patent No.: US 9,629,599 B2
(45) Date of Patent: Apr. 25, 2017

(54) IMAGING DEVICE, ASSIGNMENT SYSTEM AND METHOD FOR ASSIGNMENT OF LOCALIZATION DATA

(71) Applicant: SIEMENS AKTIENGESELLSCHAFT, Munich (DE)

(72) Inventors: Anna Jerebko, Hausen (DE); Michael Kelm, Erlangen (DE); Michael Suehling, Erlangen (DE); Michael Wels, Bamberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 134 days.

(21) Appl. No.: 14/204,701

(22) Filed: Mar. 11, 2014

(65) Prior Publication Data

US 2014/0254910 A1   Sep. 11, 2014

(30) Foreign Application Priority Data

Mar. 11, 2013   (EP) .................................... 13158610

(51) Int. Cl.
*G06K 9/00*   (2006.01)
*A61B 6/00*   (2006.01)
(Continued)

(52) U.S. Cl.
CPC ............ *A61B 6/5211* (2013.01); *A61B 6/502* (2013.01); *G06T 7/0012* (2013.01); *G06T 7/344* (2017.01);
(Continued)

(58) Field of Classification Search
None
See application file for complete search history.

(56) References Cited

U.S. PATENT DOCUMENTS

| 6,987,831 B2 * | 1/2006 | Ning ...................... A61B 6/032 378/20 |
| 8,634,610 B2 * | 1/2014 | Kontos .................. A61B 6/502 382/115 |

(Continued)

FOREIGN PATENT DOCUMENTS

WO   WO 2012116746 A1 *   9/2012   ........... G06T 7/0012

OTHER PUBLICATIONS

Yao et al (NPL: "Predicting Breast Cancer Survivability Using Random Forest and Multivariate Adaptive Regression Splines" IEEE, Aug. 2011, hereafter referred to as Yao).*

(Continued)

*Primary Examiner* — Oneal R Mistry
(74) *Attorney, Agent, or Firm* — Laurence Greenberg; Werner Stemer; Ralph Locher (57) ABSTRACT

A method of assigning first localization data of a breast of a patient derived from first image data of the breast, the first image data being the result of a first radiological data acquisition process, to second localization data of the same breast derived from second image data, the second image data being the result of a second radiological data acquisition process, or vice versa. Thereby, the first localization data are assigned to the second localization data by intermediately mapping them into breast model data representing a patient-specific breast shape of the patient and then onto the second image data—or vice versa, thereby deriving assignment data. An assignment system performs the above-described method.

13 Claims, 9 Drawing Sheets

(51) Int. Cl.
*G06T 7/00* (2017.01)
*G06T 7/33* (2017.01)

(52) U.S. Cl.
CPC .............. *G06T 2207/10112* (2013.01); *G06T 2207/30068* (2013.01)

(56) References Cited

U.S. PATENT DOCUMENTS

| | | | | |
|---|---|---|---|---|
| 8,977,018 | B2* | 3/2015 | Buelow et al. | 382/128 |
| 2008/0144940 | A1* | 6/2008 | Russakoff | 382/203 |
| 2012/0114213 | A1* | 5/2012 | Buelow et al. | 382/131 |
| 2014/0044333 | A1* | 2/2014 | Barth et al. | 382/131 |
| 2014/0056502 | A1* | 2/2014 | Twellmann et al. | 382/131 |

OTHER PUBLICATIONS

Van Schie Guido et al; "correlating locations in ipsilateral breast tomosynthesis views using an analytical hemispherical compression model"; Institute of Physics Publishing, Physics in Medicine and Biology, Bristol; vol. 56; No. 15; pp. 4715-4730; ISSN: 0031-9155; DOI: 10.1088/0031-9155/56/15/006; XP 020208289; 2011; GB; Jul. 8, 2011.

Wels Michael et al; "Data-Driven Breast Decompression and Lesion Mapping from Digital Breast Tomosynthesis"; Medical Image Computing and Computer-Assisted Intervention Miccai, Springer Verlag; pp. 438-446; ISBN:978-3-642-33414-6; XP047020205; 2012; Oct. 1, 2012.

Hopp T. et al; "Automatic multimodal 2D/3D breast image registration using biomechanical FEM models and intensity-based optimization"; Medical Image Analysis; vol. 17; No. 2; pp. 209-218; ISSN: 1361-8415; DOI: 10.1016/j.media.2012.10.003; XP055075729; 2013; Feb. 1, 2012.

Ghesu, Florin Cristian: Pectoral Muscle Detection in Mediolateral-Oblique Images from Mammography and Digital Breast Tomosynthesis. B.A. thesis. Lehrstuhl für Mustererkennung (Informatik 5), Friedrich-Alexander-Universität Erlangen-Nürnberg 2012.

\* cited by examiner

IMAGING DEVICE, ASSIGNMENT SYSTEM AND METHOD FOR ASSIGNMENT OF LOCALIZATION DATA

CROSS-REFERENCE TO RELATED APPLICATION

This application claims the priority, under 35 U.S.C. §119, of European application EP13158610, filed Mar. 11, 2013; the prior application is herewith incorporated by reference in its entirety.

BACKGROUND OF THE INVENTION

Field of the Invention

The present invention concerns a method of assigning first localization data of a breast of a patient derived in first image data of the breast, the first image data being the result of a first radiological data acquisition process, to second localization data of the same breast derived in second image data. The second image data being the result of a second radiological data acquisition process, or vice versa. The invention also concerns an assignment system for such purpose.

Since recently, digital breast tomosynthesis (DBT) has been increasingly replacing common two-dimensional (2D) mammography for differential diagnosis and is in discussion for screening purposes, too. DBT provides three-dimensional (3D) image volumes of the compressed human breast which are reconstructed from several (multiple) 2D projections acquired at different (i.e. varying) angles. Being a 3D imaging modality DBT naturally allows superior spatial localization of suspicious lesions.

Figure 1:
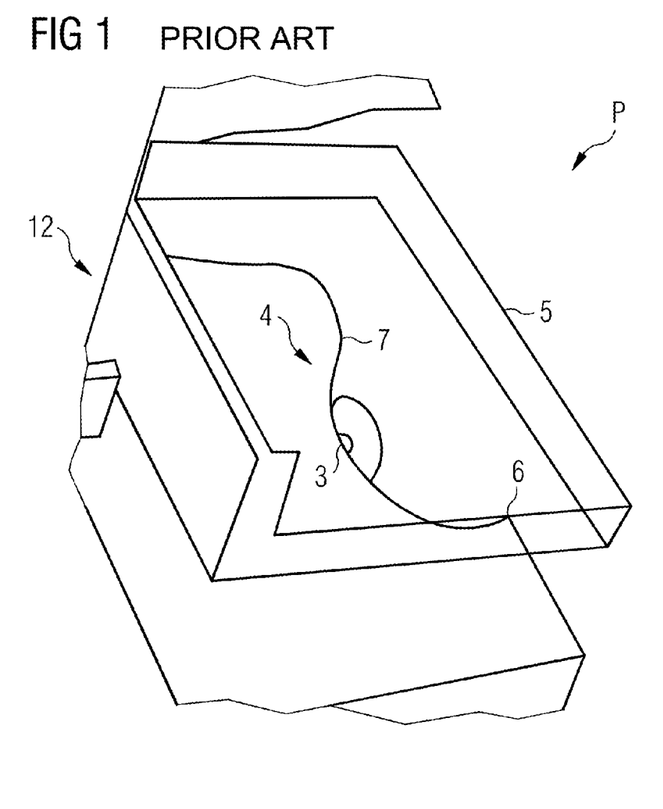
FIG. 1 is a perspective view of a mammography device according to the prior art.

FIG. 1 shows a mammography device 12 as is standard in medical practice for the generation of image data of a breast 4 of a patient P. In particular, such mammography devices 12 are used to generate DBT image data. The breast 4 is immobilized and compressed by a mechanical mechanism, the so-called paddle 5. In an exemplary manner FIG. 1 shows a positioning of a patient P in the so-called mediolateral-oplique (MLO) position. In addition, a papilla 3, a top of the breast 7 and a inframammary fold 6, which in medical practice is also called the inframammary crease or line 6, are shown.

With such a mammography device 12 in a first orientation, a first MLO scan can be carried out. After that, a second scan can be acquired in a craniocaudal (CC) direction during an examination. A CC scan implies that the breast is compressed in feet/head direction of the patient P and an MLO scan implies that the direction of compression is rotated by approximately 45° to the left or right depending on which of the two breasts is examined.

Figure 2:
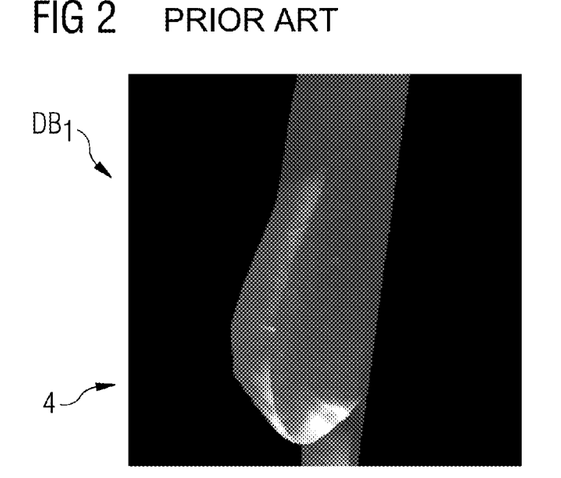
FIG. 2 is a volume rendered 3D DBT image of a breast of FIG. 1 according to the prior art.
Figure 3:
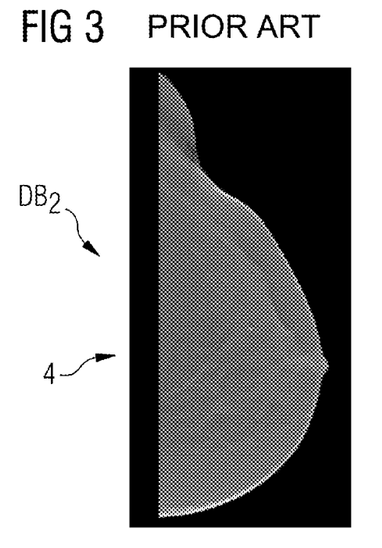
FIG. 3 is a slice of a 3D DBT image of the same breast as in FIGS. 1 and 2 according to the prior art.

FIG. 2 shows result data DB1 of a volume-rendered 3D DBT MLO scan of the breast 4 whereas FIG. 3 shows the result data DB2 of a 3D DBT CC scan of the same breast 4 in the form of one slice of the DBT data.

For the ease of navigation during reading DBT data in a (for instance standard) viewing tool it is desirable to quickly retrieve suspicious areas identified in the MLO scan in the complementary CC scan and vice versa. It is desirable to support the radiologist in assessing these findings in a holistic manner without the need for lengthy user interaction. As a result, the radiologist's workflow can remain focused on the medical question at hand and is optimized in terms of patient throughput.

This approach is referred to as "ipsilateral mapping" between different DBT views, whereby the interior of a deformed breast is volumetrically mapped to the interior of the same but differently deformed breast. More generally speaking, this approach relates to an assignment of first and second image data onto each other, as mentioned in the introductory paragraph.

A system addressing the problem is described in the article by van Schie, G. et al., entitled: CorrelatingLocations in Ipsilateral Breast Tomosynthesis Views Using an Analytical Hemispherical Compression Model", Phys. Med. Biol. 56 (15), 4715-4730 (2011). There, corresponding regions from ipsilateral 3D DBT views (MLO and CC) are matched. Thereby, the behavior of breasts—that are assumed to be hemispheres—under compression/decompression is explicitly modeled and simulated by approximating breast tissue properties. Regions are mapped by intermediately mapping them to a decompressed version of a simply hemispherical geometrical model that has been matched to the compressed breast before. The matching region in the ipsilateral view is finally found after rotation and repeated simulative compression. This method suffers from its computational complexity. Also, the chosen intermediate representation for ipsilateral mapping appears too simplistic to achieve sufficient mapping accuracy.

SUMMARY OF THE INVENTION

It is thus an object of the present invention to provide an improved possibility of assigning first and second localization data to one another, i.e. an improved possibility of ipsilateral mapping, which preferably overcomes the above-mentioned problems of the mentioned state of the art.

Thus, according to the invention, the method outlined in the introductory paragraph is characterized by the fact that the first localization data are assigned to the second localization data by intermediately mapping them into breast model data representing a patient-specific breast shape of the patient and then onto the second image data or vice versa, thereby deriving assignment data.

Throughout this application, it is to be understood that the breast of the patient is particularly a human breast (although animal breasts, in particular breasts of mammals, can be inspected as well in the context of the invention) and most particularly a female breast. Yet it may be noted that breasts of male patients can be of interest as well as for instance breast cancer contrary to the common belief can also affect men.

The first and/or second image data of the breast may contain image data of the full breast but also of parts thereof, depending mainly on the purpose of the radiological data acquisition processes and to some extent also on the abilities of the radiologists and/or the anatomical peculiarities of the patient.

As for the localization data, these may firstly contain landmarks such as natural landmarks and/or artificially generated landmarks: amongst the natural landmarks there count the position of the papilla of the breast, in particular the center of the papilla, but also other positions or lines such as the top of the breast and the inframammary fold (as mentioned above). Artificially generated landmarks can be considered such landmarks that are generated by a computer system to represent the breast, in particular to represent the outer surface (or skin) of the breast. Alternatively or additionally, the localization data may secondly contain target objects of the breast, in particular (but not restricted to) in the inside of the breast, i.e. below its surface. The position of such target objects, for instance lesions or other deviations from the normal (i.e. healthy) structure of the breast, can be described in dependence of other localization data, in particular in dependence of the above-mentioned landmarks.

The assignment process can also be considered a mapping process so that throughout this application "mapping" is considered to be an equivalent of "assigning" unless explicitly stated otherwise.

Like in the state of the art, this assignment process implies the use of a breast model onto which the localization data from the one image data are intermediately mapped before being transferred from the breast model to the other localization data of the other image data. However, the breast model used for that purpose is not a simple hemispheric model but a patient-specific one instead. The intermediately used breast model data are patient-specific since they rely on a machine learning-based, data-driven method for shape prediction from the first and/or second image data. Thus, unlike in the prior art, no explicit biomechanical modeling (and simulating) of deformations is used. As no biomechanical modeling and associated simulation is involved, the method according to the invention also does not require a GPU implementation for real-time applications. Such fast implementations are typically needed as biomechanical modeling involves computationally expensive step-wise simulation of tissue deformation.

As will be shown below, patient-specific 3D breast modeling is a rather new achievement of medico-technical science and has the effect that despite a huge number of input data from image data of a breast it is still possible to generate rather precise models of the very breast of that patient.

First, this enhancement of ipsilateral mapping has the great advantage of a much higher precision of mapping. The more refined the modeling method to achieve the patient-specific breast model is the more precise can the mapping (or assignment) of the localization data be.

Second, the method can still be carried out more effectively and with astonishingly less effort than according to the above-mentioned state of the art. This is due to the fact that the realistic input data need not first be aligned with a standard and thus unrealistic model but can rather be transferred into "their own" model instantaneously, i.e. directly and in a completely data-driven way.

Further, the same or a similar breast modeling method can be used when going further from the breast model data to the localization data in those image data onto which the firstly used image data are to be mapped—such modeling method can then simply be reversed in order to achieve an accurate and rather rapid ipsilateral mapping overall.

According to the invention, the above-mentioned assignment system contains an assignment unit which in operation assigns the first localization data to the second localization data by intermediately mapping them into breast model data representing a patient-specific breast shape of the patient and then onto the second image data—or vice versa, thereby deriving assignment data.

In other words, the assignment unit carries out the above-mentioned assignment step of the method according to the invention.

The invention further concerns an imaging device with an image data acquisition unit and with an assignment system according to the invention.

The imaging device according to the invention, the assignment system according to the invention, in particular its assignment unit (but also other components of the assignment system which will be mentioned below) may be partially or wholly accomplished by hardware components, for example using semiconductor chips such as ASICs (Application Specific Integrated Circuits), FPGAs (Field Programmable Gate Arrays), or PLAs (Programmable Logic Arrays). They may, however, also be comprised of software components or combinations of hardware and software components. Therefore, the invention also concerns a computer program product which can be loaded directly into the memory of a programmable assignment system, by program code, in order to execute a method according to the invention, when the program is executed in the assignment system.

Particularly advantageous embodiments and features of the invention are given by the dependent claims, as revealed in the following description. Thereby, features revealed in the context of the method may also be realized in the context of the products and vice versa, unless the contrary is explicitly stated.

According to a preferred embodiment of the method according to the invention the first and/or second localization data of the first and/or second image data are transformed to be integrated into the breast model data. This can be realized in the form of third localization data within the breast model data which represent the first and/or second localization data whereby the formers' positions in the breast model data correspond to the latter's position in the respective image data. In other words, not only the image data are mapped, but also their localization data. This way, the complete mapping process, i.e. also the mapping of the localization data themselves goes via the breast model data. This implies an even more increased exactness of the mapping process overall.

To carry out such method the assignment system according to the invention also contains a localization data transformation unit realized to transform the localization data of the first and/or second image data to be integrated into the breast model data.

It is particularly preferred that the first image data and/or the second image data are transformed into the breast model data using a breast modeling method. For such purpose, the assignment system contains an image data transformation unit realized to transform the first image data and/or the second image data using a breast modeling method into the breast model data. This image data transformation unit may be comprised in a common unit together with the (optional) above-mentioned localization data transformation unit or both these units may be indeed the same unit used for the two different purposes.

The breast modeling method may be chosen from a variety of methods all of which must have in common to generate patient-specific breast model data rather than artificial, non-personalized models.

A preferred breast modeling method is based on breast shape data from a database of empirical breast shape data of a plurality of breast samples. In other words, the generation of breast model data of one particular person is based on experience with previously inspected persons. The plurality of breast samples of these persons may already be pre-selected, for instance comprise only breast samples of persons of the same gender as the patient currently under inspection. Other selection criteria (such as age, diagnosis etc.) may be considered as well, additionally or alternatively. Based on such empirical data, the generation of the individual, i.e. patient-specific, breast model data, is easier to accomplish and can be even more refined. For example, the assignment system can select for instance derived from assumptions relating to the first and/or second image data from the database one particular breast shape or a particular average breast shape and then compare that selected breast shape with the first and/or second image data. This way, the patient-specific breast model data can be described in terms of deviations of the selected breast shape, whereby the breast model (data) can generally be identified as the selected breast model (i.e. breast model data thereof) plus a deviation coefficient. Such modeling is mathematically relatively easy and thus requires relatively little computational power.

A particularly preferred breast modeling method can be summarized by the below described steps in which the breast model data are modeled determination of a set of a defined plurality of input feature values, such as pixels, in the first and/or second image data. A prognostic determination of a set of target form parameters of a target form model with a defined plurality of target form parameters by means of a data-driven regression method from the plurality of input feature values are generated, wherein the plurality of target form parameters is smaller than the plurality of input feature values. A determination of the breast model data from the set of target form parameters is performed, whereby preferably the regression method is embodied as multiple, multivariate random forest regression.

This method and its advantages (amongst others a high degree of precision and accuracy whilst comparatively little computational power is necessary) is also described in more detail in an article by Wels, M., et al., entitled: Data-Driven Breast Decompression and Lesion Mapping from Digital Breast Tomosynthesis", Proceedings of the 15th International Conference on Medical Image Computing and Computer-Assisted Intervention (MICCAI 2012), Part I, LNCS 7510, pp. 438-446, 2012. This reference and its teachings are hereby incorporated in the present application. Like the method according to the invention, the breast modeling method according to this paper can be designed as entirely data-driven and based on machine-learning methods rather than on pre-defined geometrical breast models such as the hemispherical model mentioned above.

In more detail, the breast modeling method consists of a first step in which a set of a defined plurality K of input feature values is determined in the first image data. "Plurality" hereinafter means a positive natural number greater than one. The set of input feature values may involve a set of two-dimensional feature values or three-dimensional feature values, for example a vector which consists of a number K of three-dimensional feature values.

Hereinafter the terms "set" and "vector" are used synonymously. Symbols for vectors and matrices are shown in bold. The input feature values in the first and/or second image data can be determined manually or in an automated fashion or also in an appropriate semi-automatic manner.

In a second step of the modeling method, a prognostic determination of a set of target form parameters of a target form model takes place with a defined plurality L of target form parameters by a data-driven regression method from the plurality K of input feature values. Advantageously the plurality L of target form parameters is smaller than the plurality K of input feature values. A mathematical model is here described as a target form model which can describe breast model data in as compact a manner as possible in order to keep the expense of determining the breast model data low so that the execution of the modeling method is possible in a particularly time-efficient and therefore cost-efficient manner. This is achieved by the target form model reproducing the properties of the breast model data with a plurality L of target form parameters, wherein the value for L is selected in such a way that the target form parameters represent the breast model data sufficiently accurately, but at the same time the value for L is lower than the plurality K of feature values of the input feature values and also lower than a plurality M of feature values such as pixels which determine the breast model data. In particular, an individual target form parameter of the target form model can also describe a plurality of feature values in the breast model data, whereby the desired efficiency is produced when determining the breast model data.

The plurality L of target form parameters from the plurality K of input feature values is determined in the modeling method by a regression method. Compared with a purely analytical method, through the use of a regression method it is possible to advantageously ensure that a set of target form parameters can be determined or at least assessed for all conceivable manifestations of breasts. Through the use of a regression method the method therefore guarantees that breast model data can be determined for all examination objects.

In particular, the regression method involves a data-driven regression method, in other words the regression method was derived from existing radiological image data, so-called training image data. Accordingly, no assumptions are made for the regression method about the properties of breast. In particular, for determining the regression method it is not necessary to determine biomechanical parameters, such as for example the elasticity of muscle tissue, in advance.

In a third step of the method according to the invention the breast model data are determined from the set of target form parameters. The target form parameters determined in the second step of the method establish the properties of the target form model so that breast model data can be easily derived from the now parameterized target form model. For example, two-dimensional breast model data can be easily generated from a parameterized three-dimensional target form model by averaging with geometric planes. These two-dimensional breast model data can then e.g. provide a surgeon with valuable help in identifying critical tissue structures when performing surgical interventions.

Particularly preferably the regression method is characterized in that it is embodied as multiple, multivariate random forest regression. If this regression is applied to a vector x with K input feature values, then end points or leaves of the regression trees which establish the vector y with its L target form parameters are determined using the regression trees provided in this regression method—starting from the roots of the regression trees. Previously established threshold values or decision-making criteria define the traversing of the regression trees from the roots of the regression trees to the leaves of the regression trees during the execution of the modeling method.

As for the first and/or second image data, these preferably contain 3D image data reconstructed from multiple 2D acquisition image data. Such is the case for instance with the above-mentioned DBT data.

It is further preferred that the first acquisition process is an MLO scan of the breast and/or the second acquisition process is a CC scan of the breast. This way, the coordinates of the resulting image data are in line with the currently used coordinates. However, it may also prove that other scan orientations may be useful, alternatively or additionally to the mentioned ones.

Furthermore, the method according to the invention is particularly useful in such settings in which the first and/or the second acquisition process is a scan of the breast in a compressed state. Such compression automatically leads to deformations of the breast, at least in part. Therefrom result shifts of selected locations (such as target objects—see above) which makes ipsilateral mapping much more difficult and which thus necessitates a high precision of the mapping method.

It may be sufficient that the breast model data contains 2D model data, for instance a plurality of patient-specific 2D slice models of the given breast. It is preferred; however, that the breast model data represent a 3D breast model. Such is particularly useful in such cases in which the first and/or second location come from a scan of the breast in a compressed state. The breast model data can generally provide a 3D reference which is easier to comprehend for the user and which is much more self-explaining than a 2D breast model would be.

Further, it is considered advantageous if the breast model data represent a breast model of the uncompressed breast. This gives the user an even better impression of the shape of the breast one which can also be counterchecked visually by simply looking at the patient after (or before or during) the data acquisition process. Such breast model of the uncompressed breast is preferably generated based on the assumption of a particular position of the patient, i.e. a particular position of the breast. For instance, such a selected position could be such that the patient lies on a patient table with the breast hanging downwards towards the patient table. Alternatively, a selected position could be with the patient standing upright. With both these mentioned positions medical practitioners are well-acquainted because the first position would be the typical one for a data acquisition in a CT or MR tomograph while the second position is the one in which the practitioner typically encounters the patient at a first inspection. Such selected positions can thus serve as good reference positions with a great recognition factor for the user.

The first image data and second image data can be displayed separately, for instance on different screens or parts of one screen, and/or consecutively. According to a preferred embodiment of the invention, the first image data and the second image data are matched to combined image data for display in the form of an image preferably one single image containing matched localization data derived from matching the first localization data and the second localization data and bringing them into a combined coordinate system. This implies that both the first and the second images are merged into one image which is based on the previous ipsilateral mapping process. Such display of the combined image can for instance be carried out as a 3D virtual image but also as 2D virtual image(s), for instance depicting slices of the breast in a pre-defined or used-selected perspective. The user is thus offered an integrated view incorporating information from both the first and second image data. This makes it yet easier for the user to get a quick and significant impression of the breast structure and possible targets including their quality and position.

In this context, it is further preferred that corresponding first location data and second location data are registered, and preferably the first image data and second image data are matched on the basis of such registration of the location data. Such registration may contain a non-rigid, image based registration as this offers more accurate registration results overall (bearing in mind the possible compression of the breast during one or two data acquisitions). In other words, the corresponding location data are approximated according to predefined registration rules in order to be matched in the combined image data.

Further, a first image resulting from the first image data and a second image resulting from the second image data can be displayed together to a user. Alternatively, the display of the first image and second image is not done at the same time but consecutively, for instance if the user explicitly chooses to change from one image to the other. In both cases, upon the user navigating along first locations based on the first localization data in the first image, second locations based on the corresponding second localization data to the first localization data can be indicated to the user in the second image or vice versa. Such (parallel or consecutive) cross-image indication of locations makes orientation easier for the user while navigating in the images.

Moreover, it is preferred that in addition to the first and second images a breast model image resulting from the breast model data is also displayed. Upon the user navigating along first and/or second locations based on the first and/or second localization data in the first and/or second image, model locations in the breast model image based on third localization data, corresponding to the first and second localization data, are then indicated to the user. This add-on uses the breast model image (which is preferably a 3D model image and/or a model image of an uncompressed breast) as a comparison and/or orientation image for the user a kind of reference of what the breast looks like in a more natural state than a compressed state. Thus the already generated breast model data are now used again for additional display purposes as well, which means that the user gets a virtually free add-on during viewing which can further support his understanding.

The method according to the invention relates to the mapping of breasts, i.e. to an area of the body which occurs in pairs in the patient. Therefore, it is possible and highly advantageous due to the reduction of calculation effort that for the second part of the pair, i.e. the second breast of the patient the method for the first part is used. Thus, the breast model data of the second breast can be mirrored in a mirror axis. This means that through this embodiment of the method according to the invention which was created for the first breast can be applied to the second breast at little expense, without the method for the second breast having to be developed in addition. If the breast model data for the left breast have been modeled the mirrored breast model data of the left breast can be used as breast model data for the right breast or vice versa.

Other objects and features of the present invention will become apparent from the following detailed descriptions considered in conjunction with the accompanying drawings. It is to be understood, however, that the drawings are designed solely for the purposes of illustration and not as a definition of the limits of the invention.

Other features which are considered as characteristic for the invention are set forth in the appended claims.

Although the invention is illustrated and described herein as embodied in a assignment of localization data, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

In the drawings, like reference numbers refer to like objects throughout. Objects in the drawings are not necessarily drawn to scale.

DETAILED DESCRIPTION OF THE INVENTION

FIGS. 1 to 3 have already been discussed above with reference to the prior art.

Figure 4:
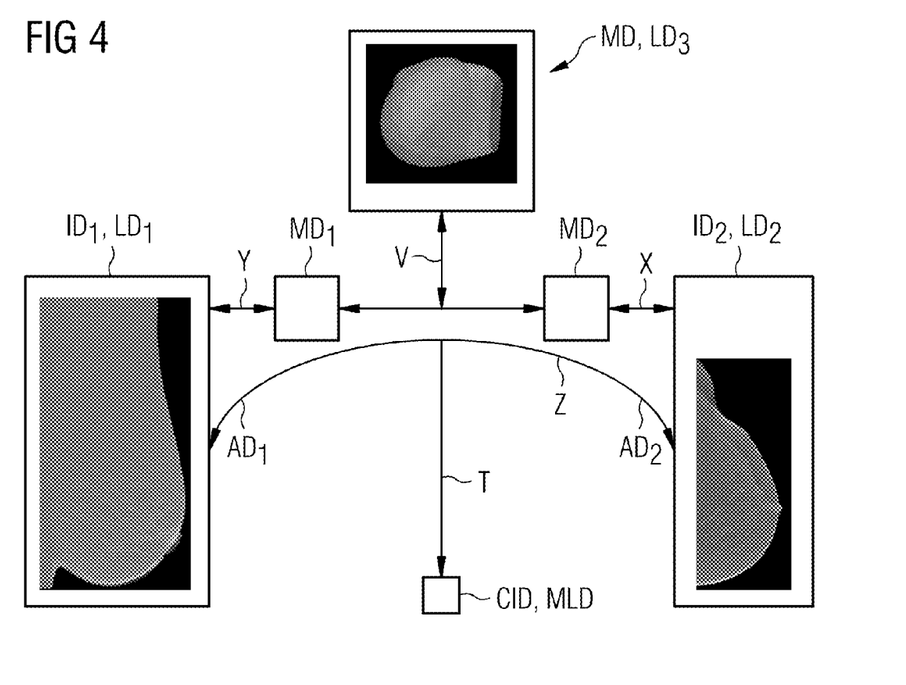
FIG. 4 is a schematic diagram of the method according to an embodiment of the invention.

Referring now to the figures of the drawing in detail and first, particularly, to FIG. 4 thereof, there is shown a schematic block diagram of the steps of a method according to an embodiment of the present invention.

First image data ID1 with first localization data LD1 are to be mapped onto second image data ID2 with second localization data LD2 in a mapping or assignment process Z. The first image data ID1 were taken of a breast 4 (see the previous figures) in a first compressed state, namely in an MLO scan, whereas the second image data ID2 were taken of the same breast 4 in a second compressed state, namely in a CC scan.

The first localization data ID1 and the second localization data ID2 each contain a number of surface landmarks which serve to describe the surface (pattern) of the breast 4 in the respective compression. The surface landmarks contain both natural landmarks such as the center of the papilla 3 of the breast 4 and of its upper and lower boundaries such as the top of the breast 7 and the inframammary fold 6, but also artificially generated surface landmarks resulting for instance from a segmentation of the breast from its surroundings (see FIGS. 5 to 13) and from a surface patterning algorithm which assigns the artificially generated landmarks relative to the natural landmarks mentioned above.

In order to ipsilaterally map in the mapping process Z the first image data ID1 onto the second image data ID2 or vice versa, use is made of an intermediate mapping model in the form of breast model data MD onto which the first image data ID1 and/or the second image data ID2 are mapped in an intermediate mapping step V. For that purpose, the first image data ID1 are mapped in a step Y by a modeling algorithm into first model data MD1 and/or the second image data ID2 are mapped in a step X by a modeling algorithm into second model data MD2. The first and second model data MD1, MD2 can already be considered breast model data—for the purpose of distinction with those breast model data eventually utilized for intermediate mapping in the context of this particular embodiment of the invention, they are simply referred to as first and second model data, rather than breast model data. An example of the modeling method (or algorithm) will be described in detail below.

The first and/or second model data MD1, MD2 represent a 3D patient-specific model of the same, but uncompressed breast 4. Further, the corresponding first and/or second localization data LD1, LD2 also mapped onto the respective model data MD1, MD2 so that therefrom result third localization data LD3. These third localization data LD3 together with the first and/or second breast model data MD1, MD2 are comprised in breast model data MD. Thus, the corresponding surface landmarks of the first and/or second localization data LD1, LD2 are defined between first and/or second image data ID1, ID2 on the one hand and the breast model data MD on the other hand for instance through canonical surface re-sampling schemes.

In a next step, coming from the breast model data MD with their third localization data LD3 mapping goes on to those image data ID1, ID2 onto which the respective other image data ID2, ID1 are to be mapped. Therefore, the breast model data MD are now mapped onto either—in a mapping step X with a reverse modeling algorithm—the second image data ID2 (if the breast model data MD have been derived from the first image data ID1) or onto—in a mapping step Y with a reverse modeling algorithm—the first image data ID1 (if the breast model data MD have been derived from the second image data ID2). This way, the first and second image data ID1, ID2 with their first and second localization data LD1, LD2 are indirectly assigned to each other via the breast model data MD. From this mapping or assignment process Z there result first and/or second assignment data AD1, AD2. In a further, optional, combination step T the first image data ID1 and the second image data ID2 are additionally matched. From this matching, there result combined image data CID for display in the form of an image containing matched localization data MLD. These matched localization data MLD are derived from matching the first localization data LD1 and the second localization data LD2 and bringing them into a combined coordinate system.

Figure 5:
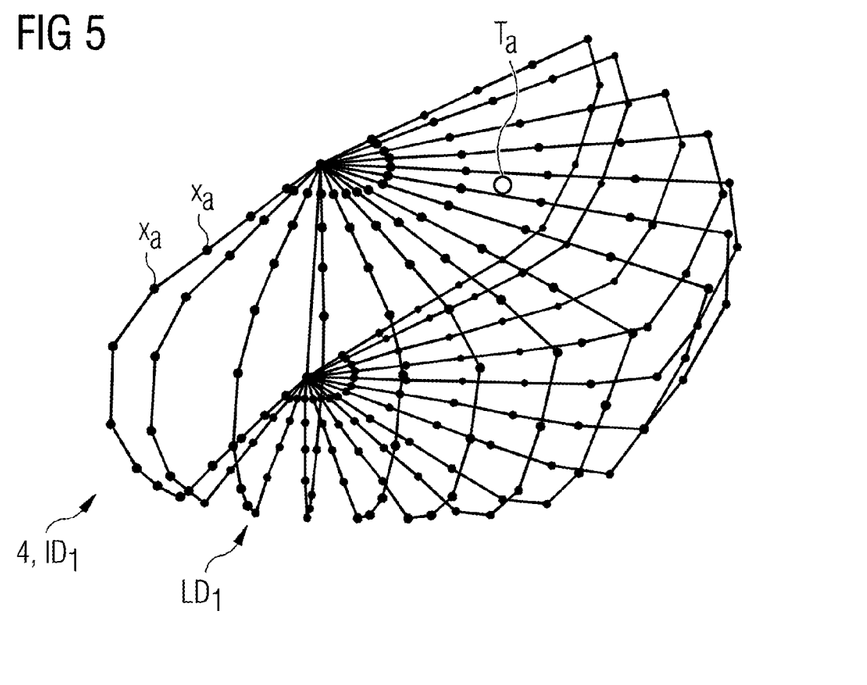
FIG. 5 is a schematic representation of a breast, images of which have been acquired in a CC scan according to the invention.
Figure 6:
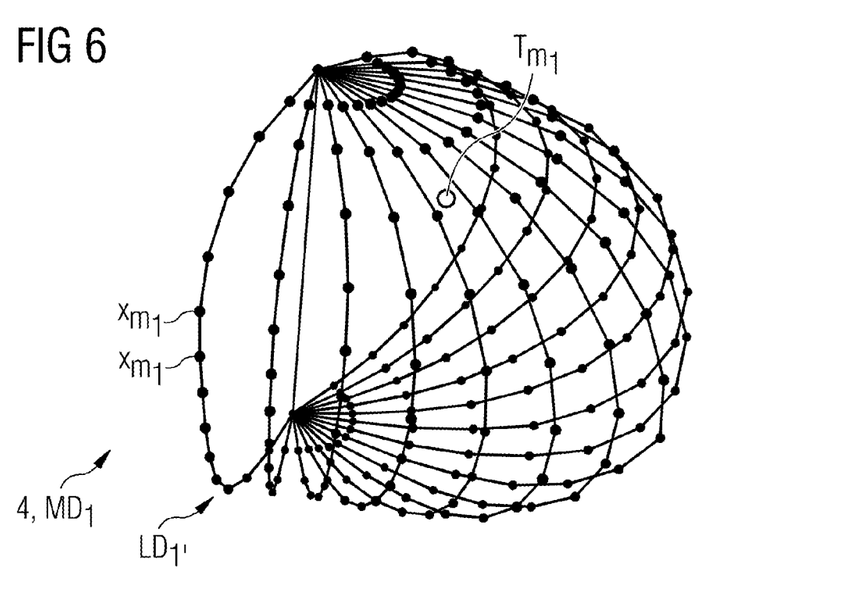
FIG. 6 is a schematic representation of a first breast model of the same breast, which has been derived from the images represented in FIG. 5.
Figure 7:
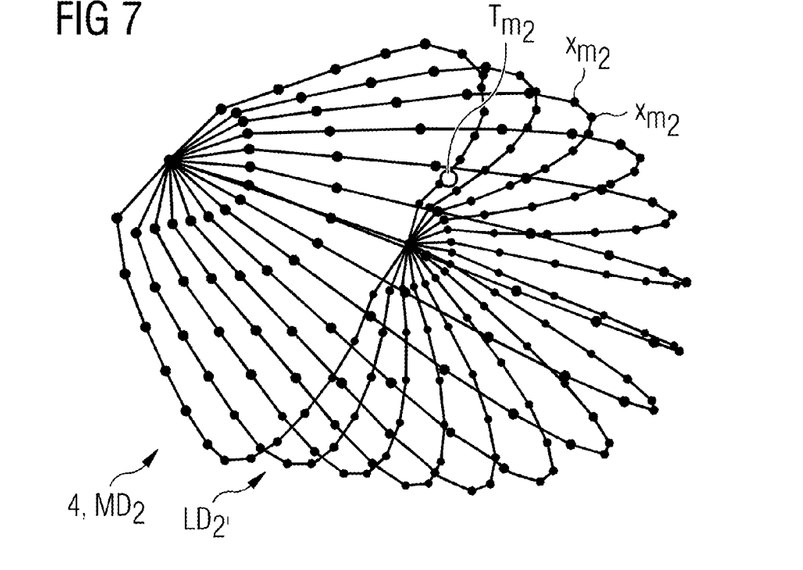
FIG. 7 is a schematic representation of a second breast model of the same breast as in FIGS. 5 and 6, corresponding to images acquired in an MLO scan.
Figure 8:
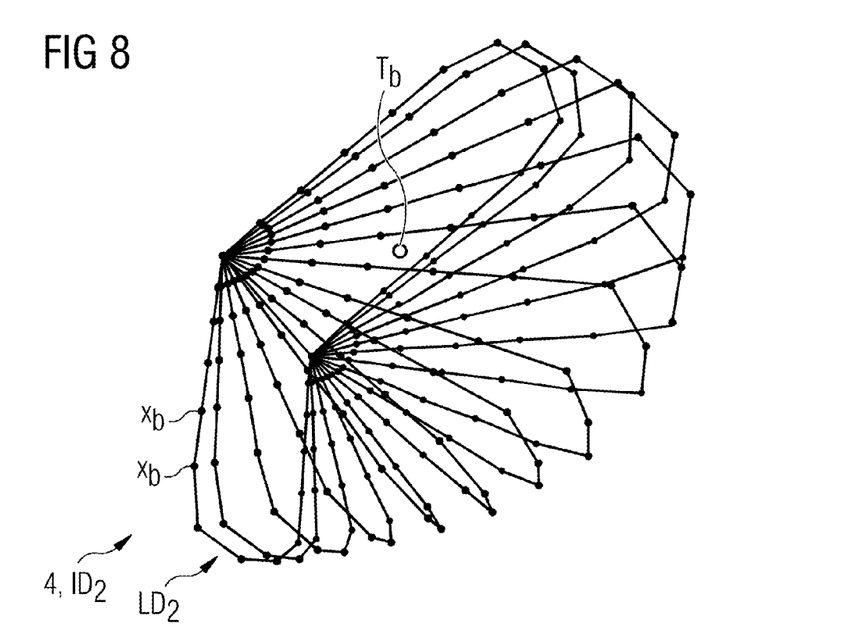
FIG. 8 is a schematic representation of the same breast as in FIGS. 5 to 7, images of which have been acquired in an MLO scan.

FIGS. 5 to 8 show four representative images of the same breast 4. The shape of the breast 4, namely its surface, is thereby represented by artificially generated surface landmarks xa, xm1, xm2, xb. A target object Ta, Tm1, Tm2, Tb within the breast 4 is also shown. In FIG. 5, first localization data LD1 contain the surface landmarks xa and the target object Ta. In FIG. 6, first model localization data LD1' contains the surface landmarks xm1 and the target object Tm1. In FIG. 7, second model localization data LD2' contain the surface landmarks xm2 and the target object Tm2. In FIG. 8, second localization data LD2 contain the surface landmarks xb and the target object Tb. It may be noted that while the landmarks xa, xm1, xm2, xb may differ from each other (as they only represent the particular shape of the breast 4 in a particular compression and/or modeling state), the target object Ta, Tm1, Tm2, Tb is the same object all throughout the FIGS. 5 to 8.

FIG. 5 shows first image data ID1 of the breast 4 which were acquired in a CC scan of the compressed breast 4. Due to the CC compression, the first image data ID1 depict a breast shape the surface of which is deformed both in the upper region and in the lower region. The target object Ta is positioned here below the surface of the breast 4 about a third of its thickness down inside of the breast 4 at the right hand side, comparatively close to the chest (not shown).

From these first image data ID1, using a breast modeling method, one can arrive at the first model data MD1 of the breast 4 in FIG. 6, which show the breast 4 in an uncompressed state in a CC orientation. The target object Tm1 appears to be in the upper quarter of the breast 4, quite in the middle along its horizontal orientation.

This first model can now be compared to (and mapped onto) a second model with corresponding second breast model data MD2 of the same breast 4 as shown in FIG. 7, which models the uncompressed breast 4 in an MLO orientation. This second model has been derived from second image data ID2 as shown in FIG. 8 which stem from an MLO scan of the compressed breast 4. The target object Tm2, Tb appears to be in quite different locations of the breast 4 which is due to the different compression and/or orientation of the breast imaging device that was used/modeled.

The succession of FIGS. 5 to 8 also indicate as an illustration how the first image data ID1 can be mapped onto the second image data ID2 or vice versa. They are mapped onto each other via an intermediate mapping onto the respective breast model data MD1, MD2 and then further to the respective other image data ID2, ID1.

Figure 9:
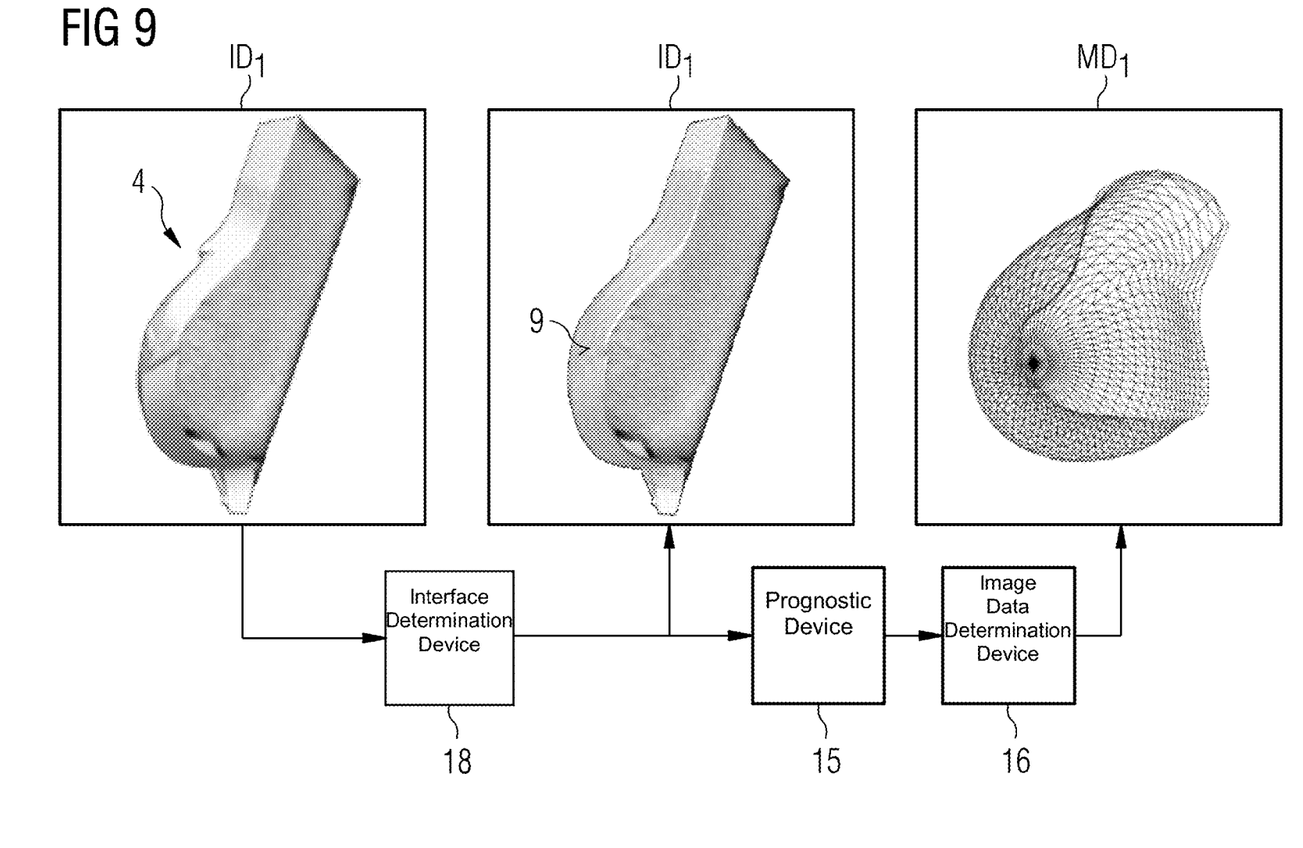
FIG. 9 is an illustration of exemplary first image data and corresponding breast model data for explanation of an embodiment of modeling method which can be used in the context of the invention.

FIG. 9 shows the first image data ID1 and the corresponding breast model data MD1 of an exemplary nature in order to explain a particularly preferred breast modeling method which can be used in the context of the method according to the invention. In particular, FIG. 9 shows how in the first image data ID1, which were already segmented, an interface 9 is determined using an interface determination device 18 as an interim step. The interface 9 in this example involves the surface of the skin of the breast 4. In addition, FIG. 9 shows the breast model data MD1, which were determined using a prognostic device 15 and an image data determination device 16. Further, FIG. 9 shows how the breast model data MD1 in a non-compressed manner can be advantageously predicted from the first image data ID1, which show the breast 4 in compressed form, without further image acquisition, i.e. completely data-driven.

As for FIGS. 10 to 13, an example of a modeling method is given with reference to modeling first model data MD1 from first image data ID1. It is to be understood, however, that the same way second model data MD2 from second image data ID2 can be modeled and that indeed the breast model data MD used in the context of the invention are then derived from the first and/or second model data MD1, MD2 by including the third localization data LD3 in them, as explained above.

Figure 10:
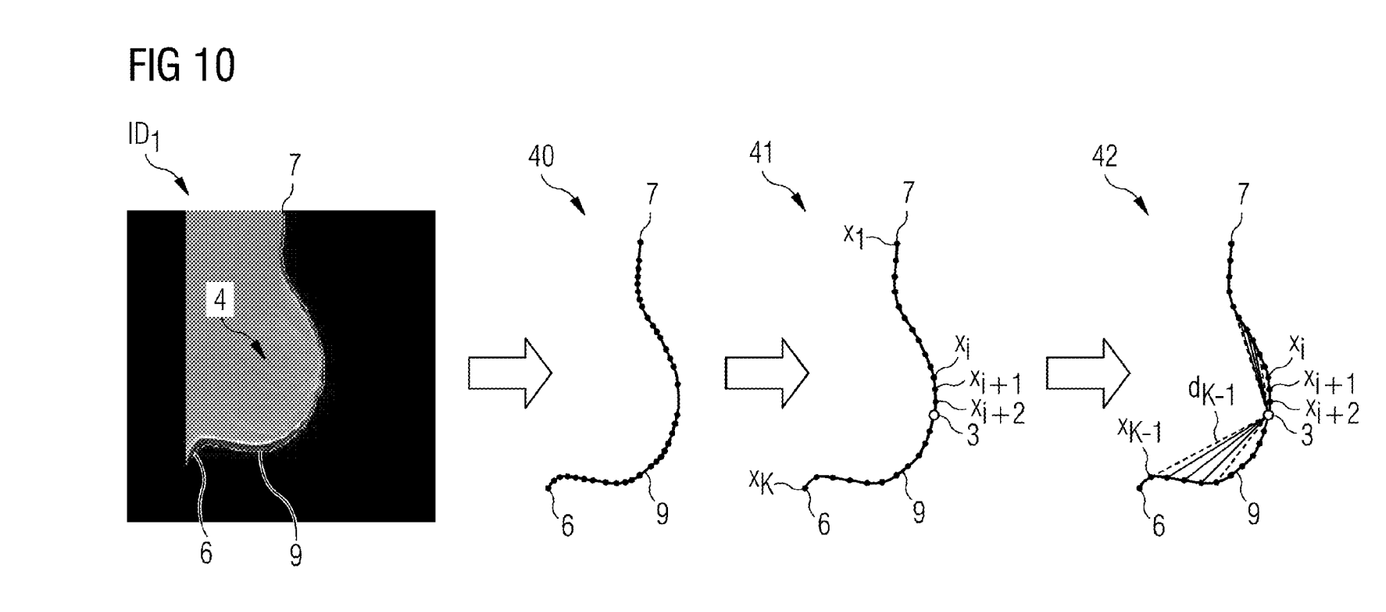
FIG. 10 is an illustration of an example of a detail of the modeling method of FIG. 9 for determining input pixels.

FIG. 10 shows the modeling method steps for determining a set of input feature values $x1, \ldots, xK$ in the first image data ID1 of the breast 4. For this purpose, in the first image data ID1 first characteristic anatomical landmarks 6, 7, 9 of the area of the body of the patient P considered are determined. The inframammary fold 6 and the top of the breast 7 are identified in the first image data ID1. This identification can take place automatically or also with the manual support of medical personnel.

Subsequently, in a first method step 40 for determining input feature values $x1, \ldots, xK$—in the given example pixels $x1, \ldots, xK$—an interface 9 is extracted which runs through the inframammary fold 6 and the top of the breast 7 and which is defined by a number of feature values (pixels). In a further method step 41 the number of feature values is modified by removing existing feature values or generating additional ones in such a way that their number corresponds to a pre-defined plurality K. Furthermore, the input feature values are positioned on the interface 9 by (for instance canonical) resampling methods, i.e. for example in such a way that they are uniformly distributed on the interface 9. In particular in this method step 41 additional landmarks can be determined, for example the papilla 3. The uniform distribution of the feature values may be selected in such a way that the feature values are arranged equidistantly between the landmarks, for example therefore equidistantly between the papilla 3 and the inframammary fold 6, or equidistantly between the papilla 3 and the top of the breast 7. This results in the input feature values $x1, \ldots, xK$. Furthermore, in a method step 42 distance vectors $d1, \ldots, dK$ are calculated between a number of landmarks and the input feature values $x1, \ldots, xK$. The distance vectors $d1, \ldots, dK$ are suitable as input variables for the prognostic, data-driven regression method for determining a defined plurality L of target form parameters $y1, \ldots, yL$.

Canonical re-sampling can also take into account the surface of the pectoral muscle. It is visible in DBT scans and can be fully automatically detected, e.g., by the method described in Ghesu, Florin Cristian: Pectoral Muscle Detection in Mediolateral-Oblique Images from Mammography and Digital Breast Tomosynthesis. B.A. thesis. Lehrstuhl für Mustererkennung (Informatik 5), Friedrich-Alexander-Universität Erlangen-Nürnberg 2012. Regarding uncompressed shapes, the pectoral muscle surface is identical with the dorsal surface of the predicted uncompressed patient-specific shape. In CC scans the rough localization of the pectoral muscle surface can be concluded from the image acquisition and positioning guidelines.

In the example shown in FIG. 10 and other figures it goes without saying that the methods and devices according to the invention are naturally also suitable for 3D first image data ID1 and 3D (breast) model data MD1 and can be used advantageously even if a 2D image was selected here for reasons of clarity. In particular, in the figures the interfaces 9 and additional planes are shown as lines on account of the image selected here—but without restricting the application of the invention.

Figure 11:
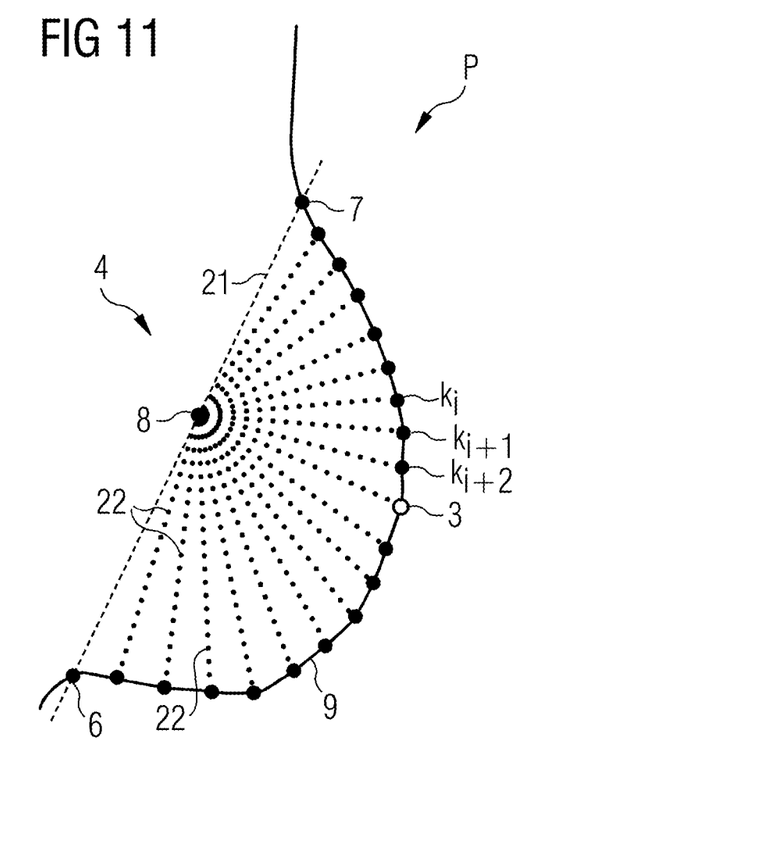
FIG. 11 is an illustration of an exemplary application of the modeling method shown in FIGS. 9 and 10 for determining curve points.
Figure 12:
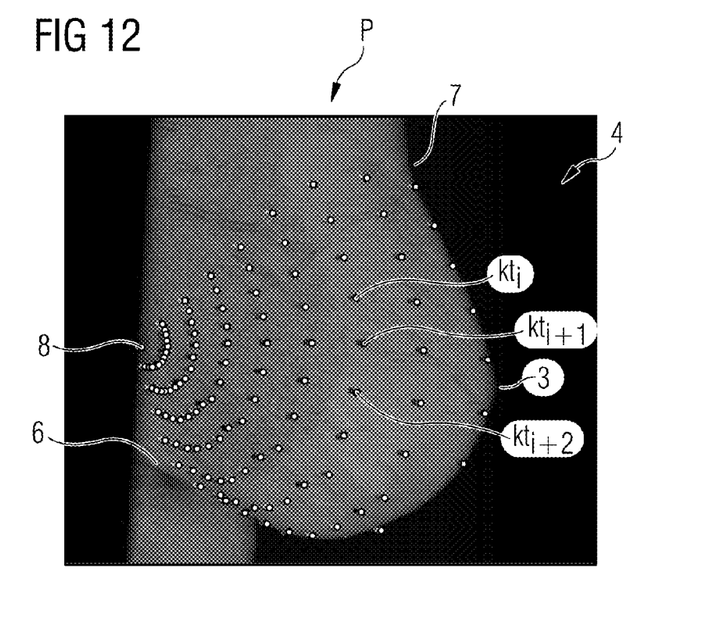
FIG. 12 is an illustration showing an example with first image data and associated contour points.

FIG. 11 provides an exemplary application of the method according to the invention for determining curve points $k1, \ldots, kK$ and the contours in the first image data ID1 and of the corresponding (breast) model data MD1 of the breast 4 of the patient P. For this purpose, firstly characteristic anatomical landmarks such as the papilla 3, the inframammary fold 6 and the top of the breast 7 are determined in the first image data ID1 and of the corresponding (breast) model data MD1. Then, a determination of an interface 9 which runs through the determined landmarks 3, 6, 7 takes place. In addition, a curve k is determined in each case, which is established by the curve points $k1, \ldots, kK$, and runs approximately in the interface 9 as well as through the anatomical landmarks 3, 6, 7. The curve points $k1, \ldots, kK$ are preferably established in such a way that they are distributed approximately uniformly on the curve. In addition, the breast plane 21 is determined, which is vertical to the MLO (and/or CC) plane and which runs through the points established by the inframammary fold 6 and the top of the breast 7. Then a projection of the papilla 3 onto the breast plane 21 takes place, by which a projection point 8 of the papilla 3 is produced. In an additional step, planes 22 which are produced by rotating the breast plane 21 around the projection point 8 are established in such a way that they run through the curve points k1, . . . , kK.

With the aid of the curve points k1, . . . , kK or of the rotated breast planes 22 determined in this way, contour points kt1, . . . , ktK can be determined in the interface 9 of the first image data ID1 by section formation between the rotated breast planes 22 and the interface 9. This is shown in exemplary fashion in FIG. 12.

Figure 13:
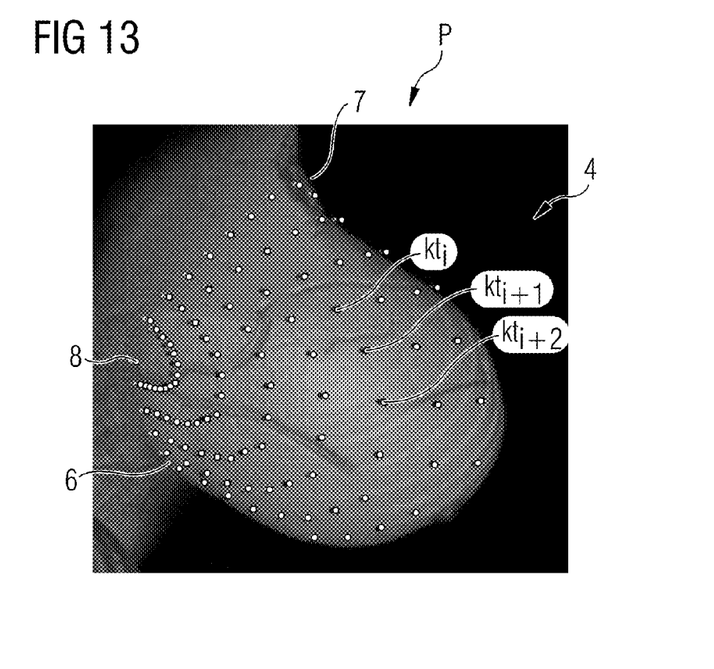
FIG. 13 is an illustration showing an example with second image data and associated contour points.

Correspondingly, FIG. 13 shows the contour points kt1, . . . , ktK in the interface 9 of the corresponding (breast) model data MD1, which were determined in turn by section formation between the rotated breast planes 22 and the interface 9. The contour points kt1, . . . , ktK in the interface 9 of the first image data ID1 and the (breast) model data MD1 can now be used to describe target objects 10, 11 (which can be considered to be target objects such as the target objects Ta, Tb, Tm1, Tm2 as shown in FIGS. 5 to 8) which are inside the breast 4. This can, for example, be achieved by a spatial thin plate spline interpolation between the contour points (i.e. any points on the contour). With the corresponding application of thin plate spline interpolation in the description of the target objects 10 in the first image data ID1 to the contours of the (breast) model data MD1, it is possible to determine the position of the target objects 11 in the (breast) model data MD1.

Figure 14:
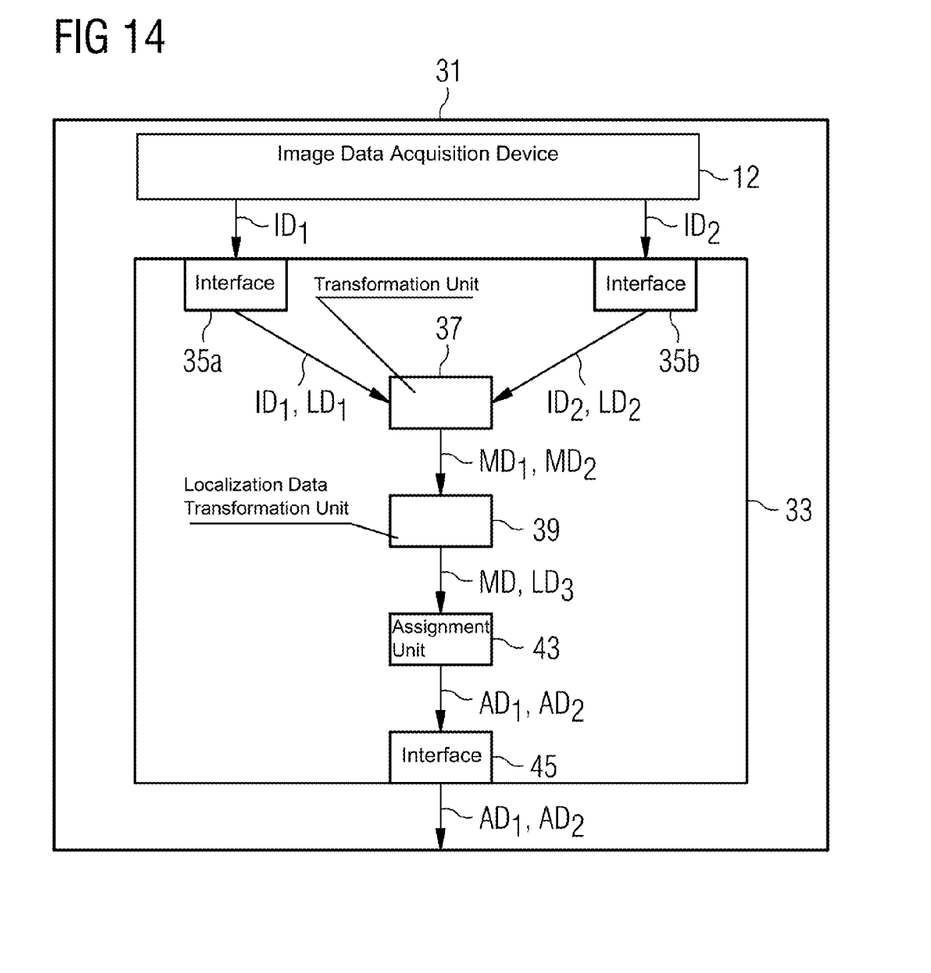
FIG. 14 is a schematic block diagram of an assignment system according to an embodiment of the invention.

FIG. 14 depicts a block diagram of an imaging device 31 according to an embodiment of the invention. It contains an image data acquisition unit 12 such as a mammography device 12 and an assignment system 33 according to an embodiment of the invention.

The assignment system 33 contains a first input interface 35a and a second input interface 35b. Further, it contains an image data transformation unit 37, a localization data transformation unit 39, an assignment unit 43 and an output interface 45.

The image data acquisition unit 12 produces the first image data ID1 and second image data ID2, i.e. with reference to the previous figures image data from an MLO scan and from a CC scan of the breast 4. These first and second image data ID1, ID2 are introduced via the two input interfaces 35a, 35b (which can indeed also be a combined or integral single input interface instead of two separate ones) into the assignment system 33. Within the assignment system 33 or even before, these first and second image data ID1, ID2 are both enriched by their localization data LD1, LD2 such as the ones mentioned above with recourse to FIG. 4. The image data transformation unit 37 transforms the first image data ID1 and/or the second image data ID2 using a breast modeling method into the first and/or second (breast) model data MD1, MD2. The localization data transformation unit 39 further transforms the first and/or second localization data LD1, LD2 of the first and/or second image data ID1, ID2 so that they are integrated into the respective (breast) model data MD1, MD2, therefrom resulting the breast model data MD containing the third localization data LD3.

Next, the assignment unit 43 assigns the first localization data LD1 to the second localization data LD2- or vice versa—by intermediately mapping them into the breast model data MD. The breast model data MD, as has previously been described, represent a patient-specific breast shape of a patient P. After the intermediate mapping, the assignment unit then maps the first image data ID1 further onto the second image data ID2—or again vice versa. Therefrom result the assignment data AD1, AD2, which are output via the output interface 45 for display and/or documentation purposes.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

The invention claimed is:

1. A method of assigning first localization data of a breast of a patient derived from first image data of the breast, the first image data being a result of a first radiological data acquisition process, to second localization data of the same breast derived from second image data, the second image data being a result of a second radiological data acquisition process, or vice versa, which comprises the step of:
    assigning the first localization data to the second localization data by intermediately mapping them into breast model data representing a patient-specific breast shape of the patient and then onto the second image data—or vice versa, thereby deriving assignment data; and
    performing the first radiological data acquisition process and the second radiological data acquisition process by scanning the breast in a compressed state;
    wherein the breast model data represent a breast model of the breast in an uncompressed state; and
    wherein the first image data resulting from the first radiological data acquisition process and the second image data resulting from second radiological data acquisition process are obtained from the same image data acquisition unit.

2. The method according to claim 1, which further comprises transforming the localization data of the first image data and/or the second image data for integration into the breast model data.

3. The method according to claim 1, which further comprises transforming the first image data and/or the second image data into the breast model data using a breast modeling method.

4. The method according to claim 3, wherein the breast modeling method is based on breast shape data from a database of empirical breast shape data of a plurality of breast samples.

5. The method according to claim 1, wherein the breast model data are modeled by the further steps of:
    determining a set of a defined plurality of input feature values in the first image data and/or the second image data, a prognostic determination of a set of target form parameters of a target form model with a defined plurality of target form parameters by means of a data-driven regression method from the plurality of input feature values, wherein the plurality of target form parameters is smaller than the plurality of input feature values; and
    determining the breast model data from the set of target form parameters, whereby the data-driven regression method is embodied as multiple, multivariate random forest regression.

6. The method according to claim 1, wherein the breast model data represent a three-dimensional breast model.

7. The method according to claim 1, which further comprises matching the first image data and the second image data thus forming combined image data for display in a form of an image containing matched localization data derived from matching the first localization data and the second localization data and bringing them into a combined coordinate system.

8. The method according to claim 7, which further comprises registering corresponding first location data and corresponding second location data, and the first image data and the second image data are matched on a basis of such registration.

9. The method according to claim 1, which further comprises displaying a first image resulting from the first image data and a second image resulting from the second image data together to a user and whereby upon the user navigating along first locations based on the first localization data in the first image, second locations based on corresponding second localization data to the first localization data are indicated to the user in the second image or vice versa.

10. The method according to claim 9, which further comprises displaying, in addition to the first and second images, a breast model image resulting from the breast model data and whereby upon the user navigating along the first locations and/or the second locations based on the first localization data and/or the second localization data in the first image and/or the second image, model locations in the breast model image based on third localization data, corresponding to the first and second localization data are indicated to the user.

11. An assignment system for assigning first localization data of a breast of a patient derived from first image data, the first image data being a result of a first radiological data acquisition process, to second localization data of the same breast from second image data derived in a second radiological data acquisition process or vice versa, the assignment system comprising:
  at least one interface for inputting the first image data and the second image data; and
  an assignment unit which in operation assigns the first localization data to the second localization data by intermediately mapping them into breast model data representing a patient-specific breast shape of the patient and then onto the second image data—or vice versa, thereby deriving assignment data;
  wherein the first radiological data acquisition process and the second radiological data acquisition process are performed by scanning the breast in a compressed state;
  wherein the breast model data represent a breast model of the breast in an uncompressed state; and
  wherein the first image data resulting from the first radiological data acquisition process is obtained from an image data acquisition unit and the second image data resulting from second radiological data acquisition process is also obtained from the image data acquisition unit.

12. An imaging device, comprising:
  an image data acquisition unit; and
  an assignment system for assigning first localization data of a breast of a patient derived from first image data, resulting from a first radiological data acquisition process performed by scanning the breast in a compressed state, to second localization data of the same breast from second image data derived in a second radiological data acquisition process performed by scanning the same breast in a compressed state or vice versa, said assignment system having an assignment unit which in operation assigns the first localization data to the second localization data by intermediately mapping them into breast model data representing a patient-specific breast shape of the patient and then onto the second image data—or vice versa, thereby deriving assignment data; and
  an image data acquisition unit for performing at least one radiological data acquisition process selected from the group consisting of the first radiological data acquisition process and the second radiological data acquisition process by scanning the breast in a compressed state;
  wherein the breast model data represent a breast model of the breast in an uncompressed state; and
  wherein the first image data resulting from the first radiological data acquisition process and the second image data resulting from second radiological data acquisition process are obtained from the image data acquisition unit.

13. A non-transitory computer readable medium having computer executable instructions stored thereon, the computer executable instructions performing a method of assigning first localization data of a breast of a patient derived from first image data of the breast, the first image data being a result of a first radiological data acquisition process, to second localization data of the same breast derived from second image data, the second image data being a result of a second radiological data acquisition process, or vice versa, which comprises the step of:
  assigning the first localization data to the second localization data by intermediately mapping them into breast model data representing a patient-specific breast shape of the patient and then onto the second image data—or vice versa, thereby deriving assignment data;
  performing the first radiological data acquisition process and the second radiological data acquisition process by scanning the breast in a compressed state;
  wherein the breast model data represent a breast model of the breast in an uncompressed state; and
  wherein the first image data resulting from the first radiological data acquisition process and the second image data resulting from second radiological data acquisition process are obtained from the same image data acquisition unit.

* * * * *